US008663981B2

(12) United States Patent
Kobinger et al.

(10) Patent No.: US 8,663,981 B2
(45) Date of Patent: Mar. 4, 2014

(54) OPTIMIZED PROMOTER SEQUENCE

(75) Inventors: Gary Kobinger, Winnipeg (CA); Heinz Feldmann, Hamilton, MT (US); Kaylie Tran, Winnipeg (CA)

(73) Assignee: Her Majesty The Queen in Right of Canada as represented by the Minister of Health, Winnipeg, Manitoba (CA)

( * ) Notice: Subject to any disclaimer, the term of this patent is extended or adjusted under 35 U.S.C. 154(b) by 162 days.

(21) Appl. No.: 13/057,529

(22) PCT Filed: Aug. 7, 2009

(86) PCT No.: PCT/CA2009/001094
§ 371 (c)(1),
(2), (4) Date: Jul. 8, 2011

(87) PCT Pub. No.: WO2010/015079
PCT Pub. Date: Feb. 11, 2010

(65) Prior Publication Data
US 2013/0158246 A1      Jun. 20, 2013

Related U.S. Application Data

(60) Provisional application No. 61/086,948, filed on Aug. 7, 2008.

(51) Int. Cl.
*C12N 15/00* (2006.01)

(52) U.S. Cl.
USPC ...................................................... 435/320.1

(58) Field of Classification Search
None
See application file for complete search history.

(56) References Cited

FOREIGN PATENT DOCUMENTS

| CA | 2553976 | 8/2005 |
| WO | WO 2006037038 A1 * | 4/2006 |
| WO | WO2006037038 | 6/2006 |

OTHER PUBLICATIONS

Kozak, Cell, 1986, vol. 44, pp. 283-292.*
Niwa et al., Gene, 1991, vol. 108, pp. 193-200.*
Calos, Nature, 1978, vol. 274, pp. 762-765.*
Cartharius et al., Bioinformatics, 2005, vol. 21, pp. 2933-2942.*
Croyle M et al "Pre clinical development of a nasal adenovirus-based vaccine against Ebola virus" Public Security S&T Summer Symposium 2008 Defence Research and Development Canada publication Jun. 9-12, 2008 CRTI 06 0204 RD pp. 93-94.
Neaumann G et al Generation of influenza A viruses entirely from cloned cDNA's Proc Natl Acad.Sci USA Aug. 1999 vol. 96 pp. 9345-9350.
Watanabek K. et al Protection against autoimmune myocarditis by gene transfer of interlleukin 10 by electroportion Circulation 2001 Vo. 104 pp. 1098-1100.
Ozawa M. et al "Contributions of two nuclear localization signals of influenza A virus nucleoprotein to viral replication"Journal of Virology Jan. 2007 vol. 81 No. 1 pp. 30-41.
Alexopoulou A N et al "The CMV early enhancer chicken B actin (CAG) promoter can be used to drive transgene expression during the differentiation of murine embryonic stem cells into vascular progenitors "BMC Cell Biology Jan. 11, 2008 vol. 9 No. 2 pp. 1-11.
Richardson J, et al Enhanced protection against Ebola virus mediated by an improved adenovirus based vaccine PloS One 23 Apr. 23, 2009 Vo. 4 No. 4 e5308 pp. 1-8.

* cited by examiner

*Primary Examiner* — Anne Gussow
*Assistant Examiner* — Mindy G Brown
(74) *Attorney, Agent, or Firm* — Michael R. Williams; Ade & Company Inc.

(57) ABSTRACT

A modified CAG promoter which is capable of driving high levels of expression of sequences of interest inserted downstream therefrom is herein described.

3 Claims, 7 Drawing Sheets pCAGalpha Sequence (SEQ ID No. 1)

```
GTCGACATTGATTATTGACTAGTTATTAATAGTAATCAATTACGGGGTCATTAGTT
CATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCA
TAGTAACGCCAATAGGGACTTTCCATTGACGTCAATGGGTGGACTATTTACGGTA
AACTGCCCACTTGGCAGTACATCAAGTGTATCATATGCCAAGTACGCCCCCTATT
GACGTCAATGACGGTAAATGGCCCGCCTGGCATTATGCCCAGTACATGACCTTA
TGGGACTTTCCTACTTGGCAGTACATCTACGTATTAGTCATCGCTATTACCATGG
GTCGAGGTGAGCCCCACGTTCTGCTTCACTCTCCCCATCTCCCCCCCCTCCCCA
CCCCCAATTTTGTATTTATTTATTTTTTAATTATTTTGTGCAGCGATGGGGGCGGG
GGGGGGGGGGGCGCGCGCCAGGCGGGGCGGGGCGGGGCGAGGGGCGGGGC
GGGGCGAGGCGGAGAGGTGCGGCGGCAGCCAATCAGAGCGGCGCGCTCCGAA
AGTTTCCTTTTATGGCGAGGCGGCGGCGGCGGCGGCCCTATAAAAAGCGAAGC
GCGCGGCGGGCGGGAGTCGCTGCGTTGCCTTCGCCCCGTGCCCCGCTCCGCG
CCGCCTCGCGCCGCCCGCCCCGGCTCTGACTGACCGCGTTACTCCCACAGGTG
AGCGGGCGGGACGGCCCTTCTCCTCCGGGCTGTAATTAGCCTAGAGCCTCTGC
TAACCATGTTCATGCCTTCTTCTTTTCCTACAGCTCCTGGGCAACGTGCTGGTT
GTTGTGCTGTCTCATCATTTTGGCAAAGAATTCGAGCTCATCGATGCATGGTACC
CGGGCATGCTCGAGCTAGCAGATCTTTTTCCCTCTGCCAAAAATTATGGGGACAT
CATGAAGCCCCTTGAGCATCTGACTTCTGGCTAATAAAGGAAATTTATTTTCATTG
CAATAGTGTGTTGGAATTTTTTGTGTCTCTCACTCGGAAGGACATATGGGAGGGC
AAATCATTTAAAACATCAGAATGAGTATTTGGTTTAGAGTTTGGCAACATATGCCA
TATGCTGGCTGCCATGAACAAAGGTGGCTATAAAGAGGTCATCAGTATATGAAAC
AGCCCCCTGCTGTCCATTCCTTATTCCATAGAAAAGCCTTGACTTGAGGTTAGAT
TTTTTTTATATTTTGTTTTGTGTTATTTTTTCTTTAACATCCCTAAAATTTTCCTTAC
ATGTTTTACTAGCCAGATTTTTCCTCCTCTCCTGACTACTCCCAGTCATAGCTGTC
CCTCTTCTCTTATGAAGATCCCTCGACCTGCAGCCCAAGCTTGGCGTAATCATGG
TCATAGCTGTTTCCTGTGTGAAATTGTTATCCGCTCACAATTCCACACAACATACG
AGCCGGAAGCATAAAGTGTAAAGCCTGGGGTGCCTAATGAGTGAGCTAACTCAC
ATTAATTGCGTTGCGCTCACTGCCCGCTTTCCAGTCGGGAAACCTGTCGTGCCA
GCGGATCCGCATCTCAATTAGTCAGCAACCATAGTCCCGCCCCTAACTCCGCCC
ATCCCGCCCCTAACTCCGCCCAGTTCCGCCCATTCTCCGCCCCATGGCTGACTA
ATTTTTTTTATTTATGCAGAGGCCGAGGCCGCCTCGGCCTCTGAGCTATTCCAGA
AGTAGTGAGGAGGCTTTTTGGAGGCCTAGGCTTTTGCAAAAAGCTAACTTGTTT
ATTGCAGCTTATAATGGTTACAAATAAAGCAATAGCATCACAAATTTCACAAATAA
AGCATTTTTTTCACTGCATTCTAGTTGTGGTTTGTCCAAACTCATCAATGTATCTT
ATCATGTCTGGATCCGCTGCATTAATGAATCGGCCAACGCGCGGGGAGAGGCG
GTTTGCGTATTGGGCGCTCTTCCGCTTCCTCGCTCACTGACTCGCTGCGCTCGG
TCGTTCGGCTGCGGCGAGCGGTATCAGCTCACTCAAAGGCGGTAATACGGTTAT
```

Figure 1-1 pCAGalpha Sequence(cont)

CCACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGA
CAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAA
GCGTGGCGCTTTCTCAATGCTCACGCTGTAGGTATCTCAGTTCGGTGTAGGTCG
TTCGCTCCAAGCTGGGCTGTGTGCACGAACCCCCGTTCAGCCCGACCGCTGC
GCCTTATCCGGTAACTATCGTCTTGAGTCCAACCCGGTAAGACACGACTTATCGC
CACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGGTAGCT
CTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAATCA
ATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCCCC
GTCGTGTAGATAACTACGATACGGGAGGGCTTACCATCTGGCCCCAGTGCTGCA
ATGATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCC
CCCATGTTGTGCAAAAAAGCGGTTAGCTCCTTCGGTCCTCCGATCGTTGTCAGA
AGTAAGTTGGCCGCAGTGTTATCACTCATGGTTATGGCAGCACTGCATAATTCTC
TTACTGTCATGCCATCCGTAAGATGCTTTTCTGTGACTGGTGAGTACTCAACCAA
GTCATTCTGAGAATAGTGTATGCGGCGACCGAGTTGCTCTTGCCCGGCGTCAAT
ACGGGATAATACCGCGCCACATAGCAGAACTTTAAAAGTGCTCATCATTGGAAAA
CGTTCTTCGGGGCGAAAACTCTCAAGGATCTTACCGCTGTTGAGATCCAGTTCG
ATGTAACCCACTCGTGCACCCAACTGATCTTCAGCATCTTTTACTTTCACCAGCG
TTTCTGGGTGAGCAAAAACAGGAAGGCAAAATGCCGCAAAAAAGGGAATAAGGG
CGACACGGAAATGTTGAATACTCATACTCTTCCTTTTTCAATATTATTGAAGCATT
TATCAGGGTTATTGTCTCATGAGCGGATACATATTTGAATGTATTTAGAAAAATAA
ACAAATAGGGGTTCCGCGCACATTTCCCCGAAAAGTGCCACCTG

Figure 1-2

Codon Optimized Ebola Glycoprotein Sequence (SEQ ID No. 2)

TAGCTTACGAACGCGTGAGCTC*GCCACCATG*GGTGTGACCGGTATCCTGCAGCTGCCGCG
TGATCGCTTCAAACGTACCTCTTTCTTTCTGTGGGTTATCATCCTGTTCCAGCGTACCTT
TTCTATCCCGCTGGGTGTTATTCATAACTCCACCCTGCAGGTGAGCGACGTTGATAAACT
GGTTTGCCGTGACAAACTGTCTTCTACCAACCAGCTGCGCTCCGTGGGCCTGAACCTGGA
AGGTAACGGTGTTGCAACCGACGTGCCGTCTGCGACCAAACGCTGGGGTTTCCGCTCCGG
TGTTCCGCCGAAAGTTGTTAACTACGAAGCGGGCGAATGGGCTGAAAACTGTTATAACCT
GGAAATCAAGAAACCGGACGGCTCCGAGTGCCTGCCGGCAGCTCCGGACGGTATTCGCGG
CTTTCCGCGCTGTCGTTACGTTCATAAAGTTAGCGGTACTGGTCCGTGCGCAGGTGACTT
TGCTTTCCACAAAGAGGGCGCGTTTTTCCTGTATGACCGCCTGGCATCCACCGTTATTTA
CCGTGGCACCACCTTCGCGGAAGGCGTTGTGGCGTTCCTGATCCTGCCGCAGGCTAAGAA
AGATTTCTTTAGCAGCCACCCGCTGCGCGAGCCGGTTAACGCGACTGAGGATCCGTCTTC
TGGTTATTACTCCACCACTATCCGTTACCAGGCAACTGGTTTCGGTACCAACGAAACTGA
ATACCTGTTCGAAGTTGATAACCTGACCTACGTTCAGCTGGAAAGCCGCTTCACTCCGCA
GTTCCTGCTGCAGCTGAACGAAACCATCTACACCAGCGGTAAACGTTCCAACACCACCGG
CAAACTGATCTGGAAAGTTAACCCGGAGATCGATACCACTATTGGTGAGTGGGCGTTTTG
GGAAACCAAGAAAAACCTGACCCGCAAAATCCGTTCCGAGGAACTGTCTTTTACCGTTGT
TTCCAACGGCGCTAAAAACATCTCCGGCCAGTCTCCGGCGCGTACCAGCAGCGATCCGGG
CACCAACACCACTACTGAAGATCACAAAATTATGGCAAGCGAAAACAGCTCTGCAATGGT
TCAGGTGCATTCCCAGGGTCGTGAAGCAGCGGTTTCTCACCTGACTACTCTGGCTACCAT
TTCTACCTCTCCGCAGTCTCTGACTACTAAACCGGGTCCGGACAACTCTACTCATAACAC
CCCGGTTTACAAACTGGACATCAGCGAAGCGACCCAGGTTGAACAGCATCATCGCCGTAC
TGATAACGACAGCACCGCGTCTGATACTCCGTCTGCGACTACCGCAGCGGGTCCGCCGAA
GGCAGAAAACACCAACACCAGCAAATCCACCGACTTTCTGGACCCGGCTACCACCACCAG
CCCGCAGAACCACAGCGAAACCGCTGGTAACAACAACACCCACCACCAGGATACCGGCGA
GGAATCCGCATCCTCTGGTAAACTGGGTCTGATCACTAACACCATCGCAGGTGTTGCTGG
TCTGATCACCGGCGGTCGTCGTACCCGCCGTGAAGCTATTGTTAACGCACAGCCGAAATG
TAACCCGAACCTGCACTACTGGACCACTCAGGATGAAGGCGCTGCTATCGGCCTGGCATG
GATCCCGTACTTCGGTCCGGCGGCTGAAGGTATCTATATCGAAGGTCTGATGCACAACCA
GGATGGTCTGATTTGCGGTCTGCGTCAGCTGGCGAACGAAACCACTCAGGCGCTGCAGCT
GTTCCTGCGCGCAACCACCGAGCTGCGTACCTTCTCTATCCTGAACCGTAAGGCGATCGA
CTTTCTGCTGCAGCGTTGGGGTGGTACCTGCCATATCCTGGGTCCGGACTGCTGTATCGA
GCCGCATGATTGGACTAAAAACATCACTGACAAAATCGACCAGATCATTCACGACTTCGT
TGACAAAACCCTGCCGGACCAGGGCGATAACGACAACTGGTGGACCGGCTGGCGTCAGTG
GATTCCGGCAGGCATCGGCGTTACCGGTGTTATTATTGCTGTGATTGCACTGTTTTGCAT
TTGCAAGTTCGTTTTCTGAGCATGCTAATAATAA

Figure 2 though not necessarily identical, expression of an operably linked gene of interest) similarly and are structurally similar (that is, retain most if not all of the sequence set forth in SEQ ID No. 1, for example, 70% or more identity or similarity as well as promoter constructs which include additional sequences as discussed above) are within the scope of the invention.

```
                        SEQUENCE LISTING

<160> NUMBER OF SEQ ID NOS: 2

<210> SEQ ID NO 1
<211> LENGTH: 3916
<212> TYPE: DNA
<213> ORGANISM: artificial sequence
<220> FEATURE:
<223> OTHER INFORMATION: modified promoter construct

<400> SEQUENCE: 1
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atgggtcgag gtgagcccca cgttctgctt cactctcccc     420 atctccccc cctccccacc cccaattttg tatttattta ttttttaatt attttgtgca     480
gcgatggggg cggggggggg ggggcgcgc gccaggcggg gcgggcggg gcgaggggcg     540 gggcggggcg aggcggagag gtgcggcggc agccaatcag agcggcgcgc tccgaaagtt     600
tccttttatg gcgaggcggc ggcggcggcg gccctataaa aagcgaagcg cgcggcgggc     660
gggagtcgct gcgttgcctt cgccccgtgc cccgctccgc gccgcctcgc gccgcccgcc     720
ccggctctga ctgaccgcgt tactcccaca ggtgagcggg cgggacggcc cttctcctcc     780
gggctgtaat tagcctagag cctctgctaa ccatgttcat gccttcttct ttttcctaca     840
gctcctgggc aacgtgctgg ttgttgtgct gtctcatcat tttggcaaag aattcgagct     900
catcgatgca tggtacccgg gcatgctcga gctagcagat cttttccct ctgccaaaaa     960 ttatggggac atcatgaagc cccttgagca tctgacttct ggctaataaa ggaaatttat    1020
tttcattgca atagtgtgtt ggaattttt gtgtctctca ctcggaagga catatgggag    1080
ggcaaatcat taaaacatc agaatgagta tttggtttag agtttggcaa catatgccat    1140
```

-continued

| | |
|---|---|
| atgctggctg ccatgaacaa aggtggctat aaagaggtca tcagtatatg aaacagcccc | 1200 |
| ctgctgtcca ttccttattc catagaaaag ccttgacttg aggttagatt tttttttatat | 1260 |
| tttgttttgt gttatttttt tctttaacat ccctaaaatt ttccttacat gttttactag | 1320 |
| ccagattttt cctcctctcc tgactactcc cagtcatagc tgtccctctt ctcttatgaa | 1380 |
| gatccctcga cctgcagccc aagcttggcg taatcatggt catagctgtt tcctgtgtga | 1440 |
| aattgttatc cgctcacaat tccacacaac atacgagccg gaagcataaa gtgtaaagcc | 1500 |
| tggggtgcct aatgagtgag ctaactcaca ttaattgcgt tgcgctcact gcccgctttc | 1560 |
| cagtcgggaa acctgtcgtg ccagcggatc cgcatctcaa ttagtcagca accatagtcc | 1620 |
| cgcccctaac tccgcccatc ccgcccctaa ctccgcccag ttccgcccat tctccgcccc | 1680 |
| atggctgact aatttttttt atttatgcag aggccgaggc cgcctcggcc tctgagctat | 1740 |
| tccagaagta gtgaggaggc ttttttggag gcctaggctt ttgcaaaaag ctaacttgtt | 1800 |
| tattgcagct tataatggtt acaaataaag caatagcatc acaaatttca caataaagc | 1860 |
| attttttca ctgcattcta gttgtggttt gtccaaactc atcaatgtat cttatcatgt | 1920 |
| ctggatccgc tgcattaatg aatcggccaa cgcgcgggga gaggcggttt gcgtattggg | 1980 |
| cgctcttccg cttcctcgct cactgactcg ctgcgctcgg tcgttcggct gcggcgagcg | 2040 |
| gtatcagctc actcaaaggc ggtaatacgg ttatccacag aatcagggga taacgcagga | 2100 |
| aagaacatgt gagcaaaagg ccagcaaaag gccaggaacc gtaaaaaggc cgcgttgctg | 2160 |
| gcgtttttcc ataggctccg ccccctgac gagcatcaca aaaatcgacg ctcaagtcag | 2220 |
| aggtggcgaa acccgacagg actataaaga taccaggcgt ttccccctgg aagctccctc | 2280 |
| gtgcgctctc ctgttccgac cctgccgctt accggatacc tgtccgcctt tctcccttcg | 2340 |
| ggaagcgtgg cgctttctca atgctcacgc tgtaggtatc tcagttcggt gtaggtcgtt | 2400 |
| cgctccaagc tgggctgtgt gcacgaaccc cccgttcagc ccgaccgctg cgccttatcc | 2460 |
| ggtaactatc gtcttgagtc aacccggta agacacgact tatcgccact ggcagcagcc | 2520 |
| actggtaaca ggattagcag agcgaggtat gtaggcggtg ctacagagtt cttgaagtgg | 2580 |
| tggcctaact acggctacac tagaaggaca gtatttggta tctgcgctct gctgaagcca | 2640 |
| gttaccttcg gaaaaagagt tggtagctct tgatccggca acaaaccac cgctggtagc | 2700 |
| ggtggttttt tgtttgcaa gcagcagatt acgcgcagaa aaaaggatc tcaagaagat | 2760 |
| cctttgatct tttctacggg gtctgacgct cagtggaacg aaaactcacg ttaagggatt | 2820 |
| ttggtcatga gattatcaaa aaggatcttc acctagatcc ttttaaatta aaatgaagt | 2880 |
| tttaaatcaa tctaaagtat atatgagtaa acttggtctg acagttacca atgcttaatc | 2940 |
| agtgaggcac ctatctcagc gatctgtcta tttcgttcat ccatagttgc ctgactcccc | 3000 |
| gtcgtgtaga taactacgat acgggagggc ttaccatctg gccccagtgc tgcaatgata | 3060 |
| ccgcgagacc cacgctcacc ggctccagat ttatcagcaa taaaccagcc agccggaagg | 3120 |
| gccgagcgca gaagtggtcc tgcaacttta tccgcctcca tccagtctat taattgttgc | 3180 |
| cgggaagcta gagtaagtag ttcgccagtt aatagtttgc gcaacgttgt tgccattgct | 3240 |
| acaggcatcg tggtgtcacg ctcgtcgttt ggtatggctt cattcagctc cggttcccaa | 3300 |
| cgatcaaggc gagttacatg atcccccatg ttgtgcaaaa aagcggttag ctccttcggt | 3360 |
| cctccgatcg ttgtcagaag taagttggcc gcagtgttat cactcatggt tatggcagca | 3420 |
| ctgcataatt ctcttactgt catgccatcc gtaagatgct tttctgtgac tggtgagtac | 3480 |
| tcaaccaagt cattctgaga atagtgtatg cggcgaccga gttgctcttg cccggcgtca | 3540 |

-continued

```
atacgggata ataccgcgcc acatagcaga actttaaaag tgctcatcat tggaaaacgt    3600
tcttcggggc gaaaactctc aaggatctta ccgctgttga gatccagttc gatgtaaccc    3660
actcgtgcac ccaactgatc ttcagcatct tttactttca ccagcgtttc tgggtgagca    3720
aaaacaggaa ggcaaaatgc cgcaaaaaag ggaataaggg cgacacggaa atgttgaata    3780
ctcatactct tcctttttca atattattga agcatttatc agggttattg tctcatgagc    3840
ggatacatat ttgaatgtat ttagaaaaat aaacaaatag gggttccgcg cacatttccc    3900
cgaaaagtgc cacctg                                                    3916
```

```
<210> SEQ ID NO 2
<211> LENGTH: 2074
<212> TYPE: DNA
<213> ORGANISM: artificial sequence
<220> FEATURE:
<223> OTHER INFORMATION: Codon-optimized nucleotide sequence for Ebola
      glycoprotein

<400> SEQUENCE: 2
```

```
tagcttacga acgcgtgagc tcgccaccat gggtgtgacc ggtatcctgc agctgccgcg      60
tgatcgcttc aaacgtacct ctttctttct gtgggttatc atcctgttcc agcgtacctt     120
ttctatcccg ctgggtgtta ttcataactc caccctgcag gtgagcgacg ttgataaact     180
ggtttgccgt gacaaactgt cttctaccaa ccagctgcgc tccgtgggcc tgaacctgga     240
aggtaacggt gttgcaaccg acgtgccgtc tgcgaccaaa cgctggggtt ccgctccgg     300 tgttccgccg aaagttgtta actacgaagc gggcgaatgg gctgaaaact gttataacct     360
ggaaatcaag aaaccggacg gctccgagtg cctgccggca gctccggacg gtattcgcgg     420
ctttccgcgc tgtcgttacg ttcataaagt tagcggtact ggtccgtgcg caggtgactt     480
tgctttccac aaagaggggcg cgttttttcct gtatgaccgc ctggcatcca ccgttattta     540
ccgtggcacc accttcgcgg aaggcgttgt ggcgttcctg atcctgccgc aggctaagaa     600
agatttcttt agcagccacc cgctgcgcga gccggttaac gcgactgagg atccgtcttc     660
tggttattac tccaccacta tccgttacca ggcaactggt ttcggtacca acgaaactga     720
atacctgttc gaagttgata acctgaccta cgttcagctg gaaagccgct tcactccgca     780
gttcctgctg cagctgaacg aaaccatcta caccagcggt aaacgttcca acaccaccgg     840
caaactgatc tggaaagtta acccggagat cgataccact attggtgagt gggcgttttg     900
ggaaaccaag aaaaacctga cccgcaaaat ccgttccgag gaactgtctt ttaccgttgt     960
ttccaacggc gctaaaaaca tctccggcca gtctccggcg cgtaccagca gcgatccggg    1020
caccaacacc actactgaag atcacaaaat tatggcaagc gaaaacagct ctgcaatggt    1080
tcaggtgcat tcccagggtc gtgaagcagc ggtttctcac ctgactactc tggctaccat    1140 ttctaccctct ccgcagtctc tgactactaa accgggtccg gacaactcta ctcataacac    1200
cccggtttac aaactggaca tcagcgaagc gacccaggtt aacagcatc atcgccgtac    1260 tgataacgac agcaccgcgt ctgatactcc gtctgcgact accgcagcgg tccgccgaa    1320 ggcagaaaac accaacacca gcaaatccac cgactttctg gacccggcta ccaccaccag    1380
cccgcagaac cacagcgaaa ccgctggtaa caacaacacc caccaccagg ataccggcga    1440
ggaatccgca tcctctggta aactgggtct gatcactaac accatcgcag tgttgctgg    1500 tctgatcacc ggcggtcgtc gtacccgccg tgaagctatt gttaacgcac agccgaaatg    1560 taaccccgaac ctgcactact ggaccactca ggatgaaggc gctgcatatcg gcctggcatg    1620 gatcccgtac ttcggtccgg cggctgaagg tatctatatc gaaggtctga tgcacaacca    1680
```

```
ggatggtctg atttgcggtc tgcgtcagct ggcgaacgaa accactcagg cgctgcagct    1740
gttcctgcgc gcaaccaccg agctgcgtac cttctctatc ctgaaccgta aggcgatcga    1800
ctttctgctg cagcgttggg gtggtacctg ccatatcctg ggtccggact gctgtatcga    1860
gccgcatgat tggactaaaa acatcactga caaaatcgac cagatcattc acgacttcgt    1920
tgacaaaacc ctgccggacc agggcgataa cgacaactgg tggaccggct ggcgtcagtg    1980
gattccggca ggcatcggcg ttaccggtgt tattattgct gtgattgcac tgttttgcat    2040
ttgcaagttc gttttctgag catgctaata ataa                                2074
```

OPTIMIZED PROMOTER SEQUENCE

PRIOR APPLICATION INFORMATION

The instant application claims the benefit of U.S. Provisional patent application 61/086,948, filed Aug. 7, 2008.

BACKGROUND OF THE INVENTION

The Kozak consensus sequence or Kozak sequence plays a major role in the initiation of translation and has the consensus gcc(A/G)ccAUGG.

The CAG promoter comprises a hybrid CMV enhancer coupled to a modified chicken β-actin promoter.

SUMMARY OF THE INVENTION

According to a first aspect of the invention, there is provided a nucleotide sequence encoding a CAG promoter sequence as set forth in SEQ ID No. 1.

According to a second aspect of the invention, there is provided a nucleotide sequence comprising the CAG promoter sequence as set forth in SEQ ID No. 1 operably linked to a nucleic acid sequence comprising a Kozak sequence and a nucleic acid sequence encoding a codon-optimized Ebola virus glycoprotein as set forth in SEQ ID No. 2.

According to a third aspect of the invention, there is provided a purified or isolated functional promoter element having at least 70% or more identity with the nucleotide sequence as set forth in SEQ ID No. 1.

BRIEF DESCRIPTION OF THE DRAWINGS

FIG. 1._pCAGalpha Sequence

FIG. 2. Codon Optimized Ebola Glycoprotein Sequence

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Figure 4:
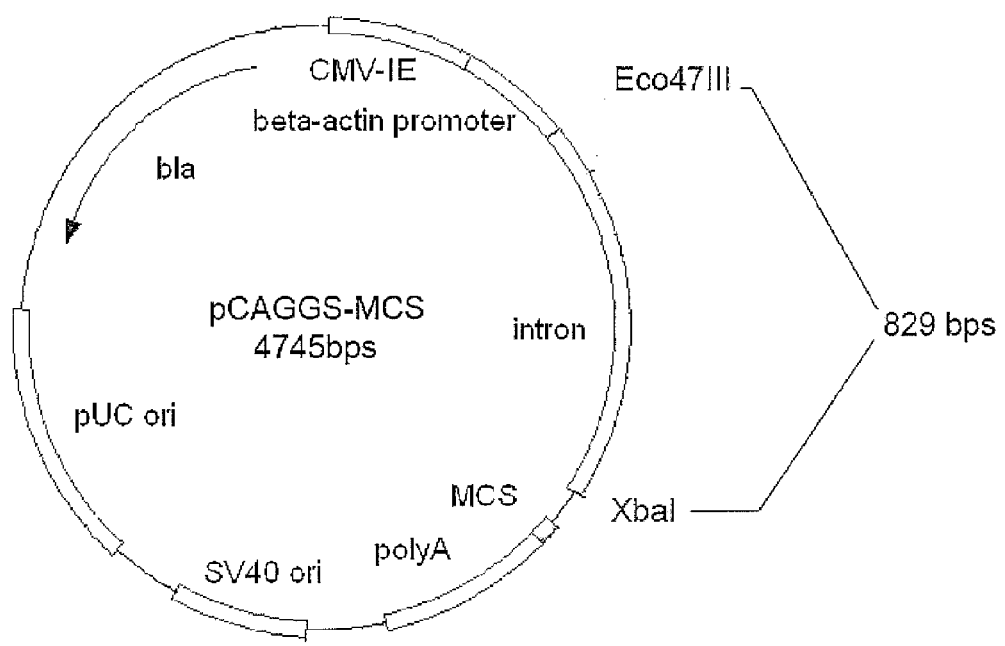
FIG. 4 shows the construction of pCAGGSΔ829. The CAG promoter of the highly efficient expression plasmid pCAGGS is comprised of a CMV-IE enhancer coupled with a modified chicken-beta actin promoter. A minimal promoter sequence was identified following a deletion of 829 base pairs in the intron region using restriction enzyme Eco47III and XbaI, we termed this vector pcag-alpha.
Figure 5:
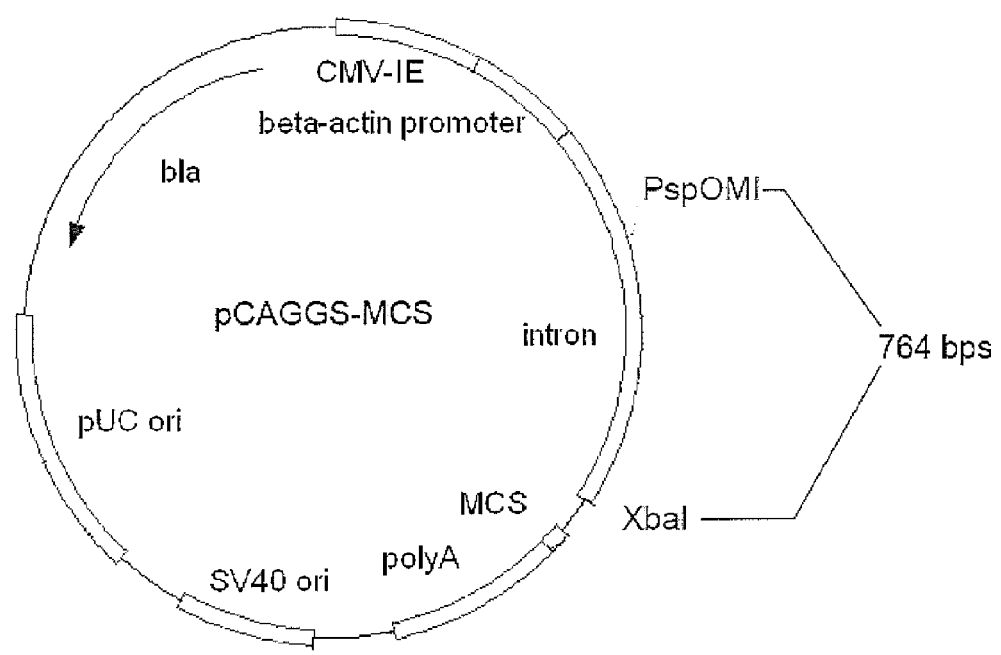
FIG. 5 shows the construction of pCAGGSΔ764. The CAG promoter of the highly efficient expression plasmid pCAGGS is comprised of a CMV-IE enhancer coupled with a modified chicken-beta actin promoter. We deleted 764 base pairs in the intron region using restriction enzymes PspOMI and XbaI. The cohesive ends were filled in and ligated together using Klenow fragment and T4 DNA ligase.
Figure 6:
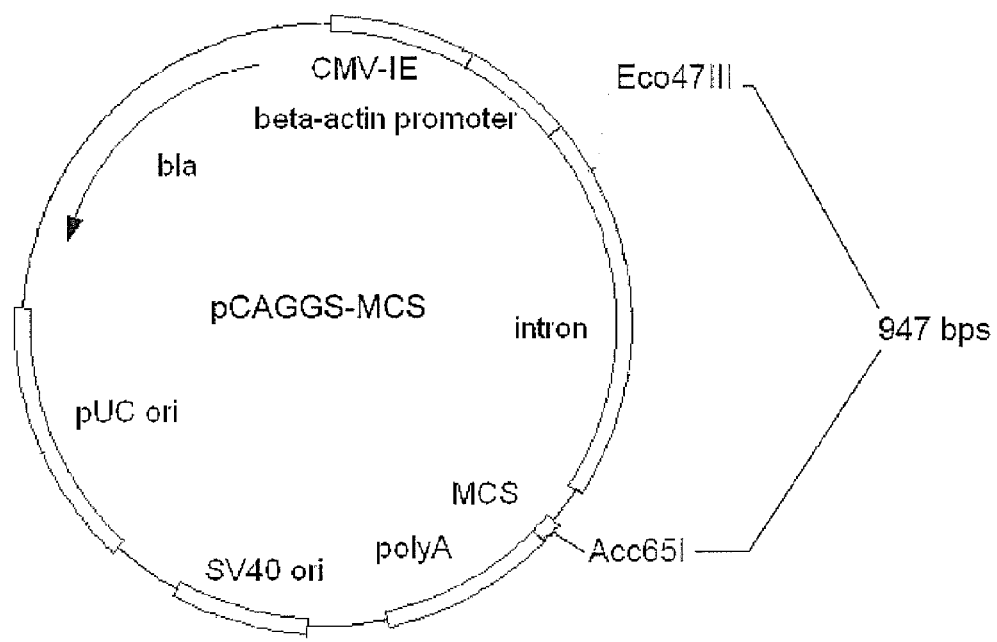
FIG. 6 shows the construction of pCAGGSΔ947. The CAG promoter of the highly efficient expression plasmid pCAGGS is comprised of a CMV-IE enhancer coupled with a modified chicken-beta actin promoter. We deleted 947 base pairs in the intron region using restriction enzymes Eco47III and Acc65I. The cohesive ends were filled in and ligated together using Klenow fragment and T4 DNA ligase

Described herein is an expression cassette comprising an optimized CAG promoter sequence (SEQ ID No. 1), shown in FIG. 1. The promoter sequence was generated by deleting 829 base pairs using restriction enyzmes Eco47III and XbaI, filling the ends with Klenow and then religated the vector carrying the CAG promoter sequence with T4 Ligase, as shown in FIG. 4. As can be seen from FIG. 3, this deletion resulted in a promoter element having greater efficiency compared to a 'wild type' construct and other constructs containing a larger deletion. The construction of the 'wild type' element is described in Niwa et al., 1991, Gene 108:193-200, which is incorporated herein by reference in its entirety, particularly for the details on the construction of the expression vector). The details of the construction of the other plasmids are shown in FIGS. 5 and 6. Specifically, FIG. 5 shows the construction of pCAGGSΔ764 in which 764 base pairs in the intron region were deleted using restriction enzymes PspOMI and XbaI. FIG. 6 shows the construction of pCAGGSΔ947 in which 947 base pairs in the intron region were deleted using restriction enzymes Eco47III and Acc65I. In both cases, the cohesive ends were filled in and ligated together using Klenow fragment and T4 DNA ligase As will be appreciated by one of skill in the art, such a promoter element can be used to drive high level expression of any gene of interest.

Figure 3:
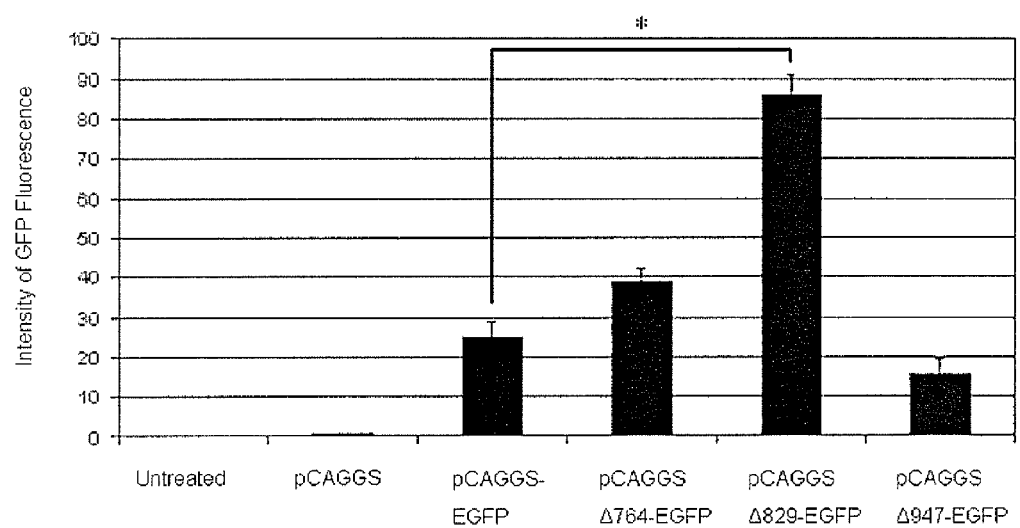
FIG. 3. Bar graphs showing expression intensity of EGFP reporter gene in transfected HEK 293T cells as determined by FACS. Portions of the 5' untranslated region of pCAGGS downstream of the CAG promoter were systematically removed generating pCAGGSΔ764-eGFP, pCAGGSΔ829-eGFP and pCAGGSΔ947-eGFP. Assays were performed in triplicate and repeated twice, the data shown is from one experiment. Error bars represent the standard deviation of the data. *p<0.001.

As will be appreciated by one skilled in the art, FIG. 3 provides considerable information useful for the construction of similar promoter cassettes. Specifically, one of skill in the art having learned that an approximately 829 base pair deletion produces a promoter having increased expression whereas the 949 base pair deletion negates this increased expression can use this information together with methods known in the art to produce related promoter cassettes without undue experimentation. For example, one of skill in the art could easily construct a series of nested deletions using any of a variety of means known in the art such as for example methods allowing progressive deletion such as nuclease-based methods, restriction enzyme digests, sub-cloning and the like to delineate the exact location of the one or more 'negative' element(s) contained within the 829 base pair deletion fragment responsible for repression of transcriptional expression as well as the location of the one or more 'positive' element(s) located between the end-points of the 829 base pair deletion fragment and the 949 base pair deletion fragment. Furthermore, one of skill in the art could also easily envision other constructs for example constructs containing a deletion that would preserve the 'phasing' or relative orientation between the upstream promoter and the transcriptional start site and/or which contained slightly larger or somewhat smaller deletions but which still retained the promoter activity described herein. It is noted that the determination of the location of the positive element could of course be easily carried out using the construct described herein. It is accordingly held that constructs such as those described above which are functionally similar, function (that is, produce a similar but not necessarily identical level of expression, for example, a promoter cassette having 10%, 20%, 25%, 35% 45%, 50%, 55%, 65%, 75%, 85%, 90%, 95%, 96%, 97%, 98%, 99% or more expression, preferably 50%, 55%, 65%, 75%, 85%, 90%, 95%, 96%, 97%, 98%, 99% or more expression when compared to the promoter cassette described herein, wherein both constructs are transformed or transfected into the same or a similar cell line and expression is detected under similar conditions) to applicant's construct.

Also described is a nucleotide sequence comprising a Kozak sequence and a nucleotide sequence encoding an Ebola virus glycoprotein. Shown in FIG. 2 is such a sequence wherein the codons encoding the Ebola virus glycoprotein have been selected so as to optimize translational efficiency of the Ebola virus glycoprotein in for example HEK 293T cells (SEQ ID No. 2).

In a preferred embodiment, the expression cassette comprises a nucleotide sequence encoding the CAG promoter sequence (SEQ ID No. 1) operably linked to a nucleic acid sequence comprising a Kozak sequence and a nucleic acid sequence encoding a codon-optimized Ebola virus glycoprotein (SEQ ID No. 2).

In a further embodiment of the invention, there is provided a purified or isolated functional promoter element having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more identity with the nucleotide sequence as set forth in SEQ ID No. 1. It is of note that the promoter is considered to be 'functional' if the promoter has 10%, 20%, 25%, 35% 45%, 50%, 55%, 65%, 75%, 85%, 90%, 95%, 96%, 97%, 98%, 99% or more expression, preferably 50%, 55%, 65%, 75%, 85%, 90%, 95%, 96%, 97%, 98%, 99% or more expression when compared to the promoter cassette described herein as SEQ ID No. 1 when operably linked to a substantially identical reporter gene, transfected into a substantially similar cell line and grown under identical conditions, typically, conditions suitable for the expression of the report gene from the promoter, that is, expression driven by the promoter.

While the preferred embodiments of the invention have been described above, it will be recognized and understood that various modifications may be made therein, and the appended claims are intended to cover all such modifications which may fall within the spirit and scope of the invention.

The invention claimed is:

1. A purified or isolated plasmid comprising a functional promoter element consisting of the nucleotide sequence as set forth in SEQ ID No. 1.

2. A purified plasmid comprising a nucleotide sequence encoding the CAG promoter sequence as set forth in SEQ ID No. 1.

3. A nucleotide sequence comprising the CAG promoter sequence as set forth in SEQ ID No. 1 operably linked to a nucleic acid sequence comprising a Kozak sequence and a nucleic acid sequence encoding the codon-optimized Ebola virus glycoprotein as set forth in SEQ ID No. 2.

* * * * *